United States Patent
Turton et al.

(10) Patent No.: US 7,642,375 B2
(45) Date of Patent: Jan. 5, 2010

(54) RADIOSYNTHESIS OF ACID CHLORIDES

(75) Inventors: David Robert Turton, London (GB); Edward Robins, London (GB)

(73) Assignee: Hammersmith Imanet Limited, London (GB)

(*) Notice: Subject to any disclaimer, the term of this patent is extended or adjusted under 35 U.S.C. 154(b) by 107 days.

(21) Appl. No.: 10/599,117

(22) PCT Filed: Mar. 18, 2005

(86) PCT No.: PCT/GB2005/001137

§ 371 (c)(1), (2), (4) Date: Jul. 20, 2007

(87) PCT Pub. No.: WO2005/090266

PCT Pub. Date: Sep. 29, 2005

(65) Prior Publication Data

US 2007/0287837 A1    Dec. 13, 2007

(30) Foreign Application Priority Data

Mar. 20, 2004 (GB) ............................. 0406315.2

(51) Int. Cl.
*C07C 51/58* (2006.01)
(52) U.S. Cl. ................................................. 562/840
(58) Field of Classification Search ............. 562/840
See application file for complete search history.

(56) References Cited

OTHER PUBLICATIONS

G.Luo, L.Xu, G.S.Poindexter, A novel solid-phase chlorinating reagent for the synthesis of acyl chlorides, Tetrahedron Letters, 2002, 43, 8909-8912.*
L.J. Wilson, "Traceless solid-phase synthesis of 2,4-diaminoquinazolines" Organic Letters, 3(4), 585-8 (2001).
A. Bongini, et.al., "Chlorination of organic compounds by means of polymer supported chlorine" J. Chem Soc., Chem. Commun., 24, 1278-9 (1980).
C.C. Leznoff & D.M. Dixit "The use of polymer supports in organic synthesis. XI the preparation of monoethers of symmetrical dixydroxy aromatic compounds" Can. J. Chem., 55(19), 3351-5 (1977).
McCarron, Julie A, et.al. "Remotely-controlled production of the 5-Ht1A receptor radioligan, {carbonyl-11C} Way-100635 via 11C-carboxylation of an immobilized grignard reagent" J. Label. Comp. Radiopharm., vol. 38, No. 10, pp. 941-953 (1996).
Luthra, S.K., et.al. "Preparation of some NCA [1-11C]Acid chlorides as labelling agents" Int'l Journal of Radiation Applications and Instrumentation part A: Applied Radiation and Isotopes, Pergamon Press Ltd. vol. 41, No. 5 (Jan. 1990) Exeter GB.
PCT/GB2005/001137 ISR/Written Opinion dated Aug. 1, 2005.
GB0406315.2 Search Report dated Aug. 13, 2004.

* cited by examiner

*Primary Examiner*—Daniel M Sullivan
*Assistant Examiner*—Sudhakar Katakam
(74) *Attorney, Agent, or Firm*—Craig Bohlken

(57) ABSTRACT

Radiolabelled acid chlorides may be synthesised by reacting a radiolabelled carboxylic acid with a solid-phase supported chlorinating agent.

23 Claims, No Drawings

RADIOSYNTHESIS OF ACID CHLORIDES

This application is a filing under 35 U.S.C. 371 of international application number PCT/GB2005/001137, filed Mar. 18, 2005, which claims priority to application number 0406315.2 filed Mar. 20, 2004, in Great Britain the entire disclosure of which is hereby incorporated by reference.

TECHNICAL FIELD OF THE INVENTION

The present invention relates to the field of radiosynthetic chemistry. In particular, the invention relates to a method for the radiosynthesis of a radiolabelled acid chloride intermediate, which can be used in the preparation of radiolabelled products such as radiolabelled amides, amines and esters.

DESCRIPTION OF RELATED ART

The established radiosynthesis of a radiolabelled acid chloride intermediate (illustrated as R—COCl below) from $CO_2$ is via the route:

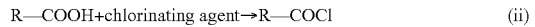

wherein R can be aromatic, short or long chain aliphatic. The chlorinating agents used, such as thionyl chloride and oxalyl chloride, need to be removed from the reaction mixture once the radiolabelled acid chloride intermediate has been formed. This is because they are very reactive and can cause chemical side reactions in any subsequent reaction in which the radiolabelled acid chloride intermediate is used. For example, when the subsequent reaction is between the radiolabelled acid chloride intermediate and an amine, the reaction between any remaining chlorinating agent and amine will result in a complex mixture and low yield of radiolabelled amide product. In addition, chlorinating agents are typically toxic and as such unsuitable where a compound is being prepared for human administration. When the radiolabelled acid chloride intermediate has a relatively low boiling point compared with the chlorinating agent, separation by distillation may be conveniently carried out [Luthra et al 1990 *Appl. Radiat. Isot.*, 41 (5) pp 471-476]. However, when the radiolabelled acid chloride intermediate has a relatively high boiling point compared with the chlorinating agent, separation by distillation from the chlorinating agent is more difficult and there is a chance that traces of chlorinating agent will remain in the final product.

To resolve the issue of separating radiolabelled acid chloride intermediates of relatively high boiling point, Luthra et al [1990 *Appl. Radiat. Isot.*, 41 (5) pp 471-476] heated the tubing between the reaction vessels and succeeded in isolating [$^{11}$C]-cyclobutanecarbonyl chloride (boiling point 140° C.) from the reaction mixture in a radiochemical yield of between 35 and 60%.

In another attempt to resolve the separation problems, e.g., McCarron et al [1996, *J. Label Comp. Radiopharms*, 38 (10), pp 941-953] used immobilised Grignard reagent in the radiosynthesis of the relatively involatile acid chloride intermediate, [carbonyl-$^{11}$C]cyclohexanecarbonyl. This meant that only small quantities of all reagents were required, thereby simplifying the purification process.

In addition to problems with removal of chlorinating agents, any separation step adds time to the radiosynthesis, leading to decay of the radioisotope, which would be desirably avoided. This is especially significant where the half-life of the radioisotope is relatively short, e.g. in the case of $^{15}$O(half-life=2.07 minutes), $^{13}$N (half-life=9.965 minutes), $^{11}$C (half-life=20.4 minutes) and $^{18}$F (half-life=109.7 minutes). Decay results in a reduction of the specific activity of the radiolabelled product overtime. Specific activity is particularly important when the radiolabelled products which are radiopharmaceuticals, as the non-radioactive cold carrier competes with the radiolabelled product. Time is therefore a reaction parameter of equal importance to chemical yield for such short-lived radiolabelled products. The relationship between time and concentration of reactants with respect to reaction kinetics is described in the literature [Långström et al, 1981, *J. Radionnal. Chem.* 64 pp 273-80].

A method for the radiosynthesis of radiolabelled acid chloride intermediates that eliminated the need for a separation step would therefore be advantageous.

SUMMARY OF THE INVENTION

The difficulties presented by the prior art methods have been surmounted by a method which uses a solid phase-supported chlorinating agent for the conversion of a radioactive carboxylic acid to a radioactive acid chloride intermediate. As the chlorinating agent is a solid reagent, there is no chlorinating agent in the final acid chloride solution. This avoids the necessity for an additional separation step such that there is no issue with residual non-radioactive chlorinating agent in the product. Furthermore, the method can be completed in less time than the prior art methods.

DETAILED DESCRIPTION OF THE INVENTION

In a first aspect the present invention relates to a method for the preparation of a radiolabelled acid chloride compound of formula (I):

wherein R is $C_1$-$C_{20}$ alkyl, $C_2$-$C_{20}$ alkenyl, $C_3$-$C_{10}$ cycloalkyl, $C_3$-$C_{10}$ heterocyclyl, $C_4$-$C_{10}$ aryl or $C_4$-$C_{10}$ heteroaryl, any of which may optionally be substituted with $NO_2$, —O($C_1$-$C_6$ alkyl), $C_3$-$C_{10}$ cycloalkyl or $C_4$-$C_{10}$ aryl;

the method comprising reacting a radiolabelled carboxylic acid of formula (II):

wherein R is as defined for formula (I);

with a solid-phase supported chlorinating agent in the presence of a base.

In the context of the present invention, the term "$C_1$-$C_{20}$ alkyl" refers to a fully saturated straight or branched hydrocarbon chain containing from 1 to 20 carbon atoms. Examples include methyl, ethyl, isopropyl, t-butyl and n-decyl. The term "$C_2$-$C_{20}$ alkenyl" refers to a straight or branched hydrocarbon chain containing from 2 to 20 carbon atoms and containing one or more C=C bonds. Examples include ethenyl, propenyl and 3-decenyl.

The term "$C_3$-$C_{10}$ cycloalkyl" refers to a cyclic fully saturated hydrocarbon group having from 3 to 6 ring carbon atoms. The cycloalkyl group may comprise either a single ring or a fused system. Examples include cyclopropyl, and cyclohexyl.

The term "$C_3$-$C_{10}$ heterocyclyl" refers to a $C_3$-$C_{10}$ cycloalkyl group as defined above but in which one of the ring carbon atoms is replaced by —S—, —O— or —NH—. Examples include tetrahydrofuranyl, morpholinyl and piperidyl.

The term "$C_4$-$C_{10}$ aryl" refers to a cyclic hydrocarbon having aromatic character and containing from 4 to 10 ring atoms. The aryl group may be a single ring, a fused aromatic system or an aromatic ring fused to a cycloalkyl or heterocyclic ring. Examples of aryl groups include phenyl, naphthyl and indolinyl.

The term "$C_4$-$C_{10}$ heteroaryl" refers to a $C_4$-$C_{10}$ aryl group as defined above but in which one of the ring carbon atoms is replaced by —S—, —O— or —NH—. Examples include pyridyl, quinolyl and indolyl.

The term "halo" refers to fluoro, chloro, bromo or iodo.

Where a compound is defined as "radiolabelled" in the present invention, this signifies that the compound comprises a radioactive isotope. The radioactive isotope may be an inherent part of the compound structure, or may alternatively be chemically attached to the compound via a suitable chemical group which optionally comprises a linker.

In the context of the present invention, a compound which is "solid-phase supported" is chemically attached to any suitable solid-phase support which is insoluble in the solvents to be used in the radiosynthesis.

Some of the solid phase supported chlorinating agents which are useful in the present invention comprise a chlorinating agent connected by a linker to a solid support. Examples of suitable solid supports include polymers such as polystyrene (which may be block grafted, for example with polyethylene glycol), polyacrylamide, or polypropylene or glass or silicon coated with such a polymer. The solid support may also be in the form of small discrete particles such as beads or pins, or a coating on the inner surface of a cartridge or on a microfabricated vessel.

In this type of structure, the solid-phase supported chlorinating agent may be, for example, a solid-phase supported acid chloride, or a solid-phase supported analogue of either thionyl chloride or oxalyl chloride. The chemical attachment of the chlorinating agent to the solid support must be such that its activity as a chlorinating agent is maintained.

Preferably, the solid-phase supported chlorinating agent is a solid-phase supported acyl chloride of Formula III:

[solid support]-linker-COCl    (III)

wherein the linker is a polyethylene glycol linker or comprises up to four groups selected from:
$C_4$-$C_{10}$ aryl or $C_4$-$C_{10}$ heteroaryl groups;
$(CH_2)_x$ groups where x is an integer from 1 to 20;
$(CH_2)_y$—O—$(CH_2)_z$ groups where y and z are integers from 1 to 20;
or combinations thereof.

In the linker groups, any $CH_2$ group may be replaced by —O—, —S—, —$SO_2$— or —$NH_2$— and the linker groups may be substituted with one or more substituents chosen from OH, halo, amino, nitro and $C_1$-$C_6$ alkoxy.

A preferred solid-phase supported acyl chloride is of Formula IIIa:

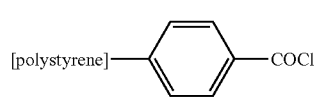

(IIa)

The above solid-phase supported acyl chloride can be prepared from commercially available polystyrene-supported carboxylic acid (Novabiochem Cat. No. 01-64-0111), by methods reported in the literature [Leznoff et al 1977 Can. J. Chem. 55 (19) pp 3351-3355; Meyers et al 1995 Molecular Diversity 1, pp 13-]. These methods describe the transformation of polystyrene-supported carboxylic acid to polystyrene-supported acyl chloride by treatment with oxalyl chloride or thionyl chloride.

Alternatively, the solid phase supported chlorinating agent may be an integral part of a polymer. For example, polymerisation of a monomer containing an acid anhydride group gives a polymer which also contains the anhydride group on every unit. Each of the anhydride groups may then be converted to two acid chloride groups by known processes, for example by heating the polymer in the presence of a chlorinating agent such as phosphorus pentachloride [Hesse et al, 1982, Liebigs Ann. Chem., 11, 2079-2086], thionyl chloride [Cantrell et al, 1977, J. Org. Chem., 42, 3562-3567] or zinc chloride [Johnson et al, 1982, J. Am. Chem. Soc., 104, 2190-2198].

An example of this process for producing solid phase supported chlorinating agents of this type include the polymerisation of anhydride monomers of type (1) by radical initiated polymerisation or monomers of type (2) by transition metal catalysed ring-opening metathesis polymerisation (ROMP)

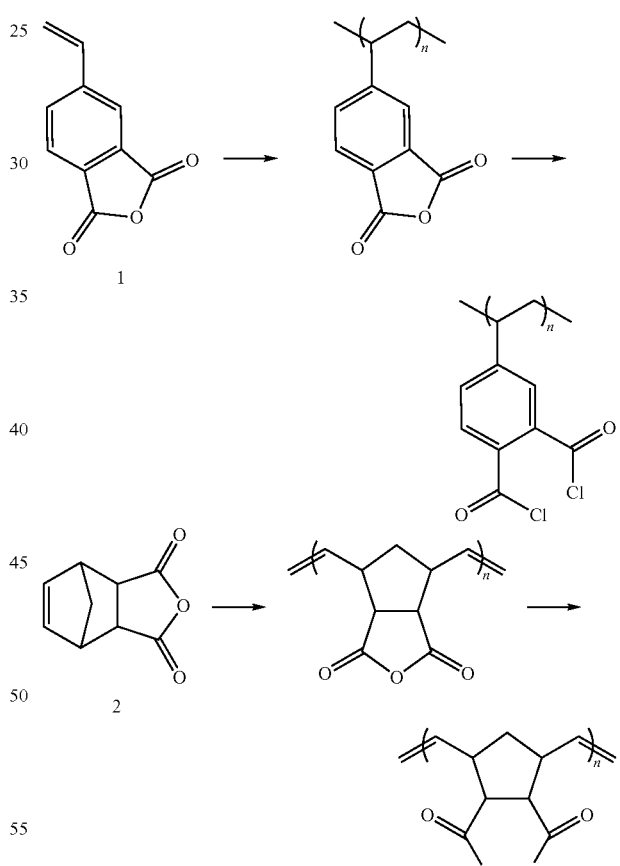

followed by their conversion to the equivalent poly(acid anhydrides).

In a similar manner an ester-containing monomer can be polymerised and the ester groups on the polymer converted to acid chloride groups by reaction with a base such as potassium hydroxide followed by reaction with a chlorinating agent such as thionyl chloride [Hagemann et al, 1997, Synth. Commun., 27, 2539-2546]

An example of this is the radical initiated polymerisation of monomers of type (3) followed by activation of the ester to the corresponding solid phase supported acid chloride.

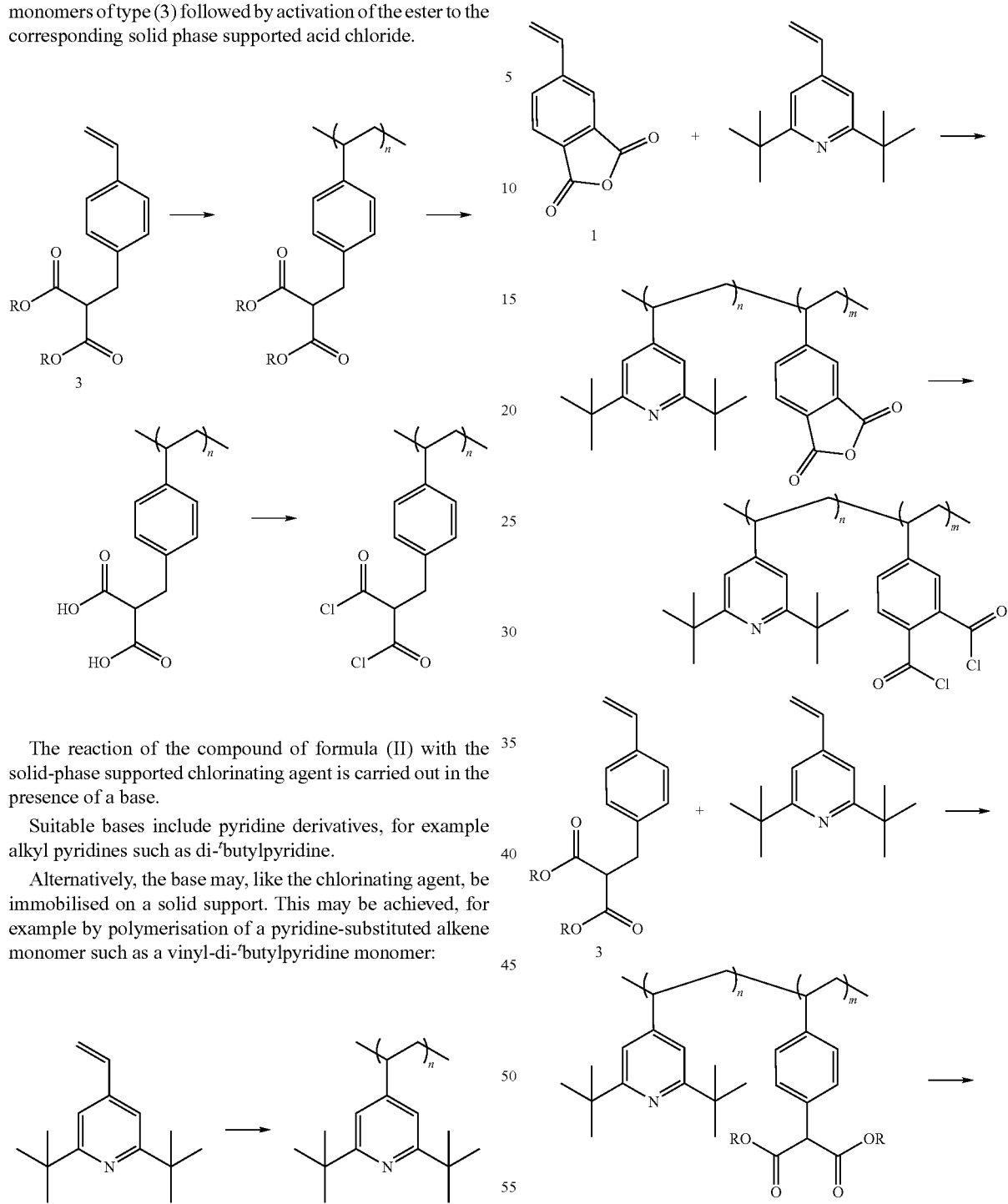

The reaction of the compound of formula (II) with the solid-phase supported chlorinating agent is carried out in the presence of a base.

Suitable bases include pyridine derivatives, for example alkyl pyridines such as di-$^t$butylpyridine.

Alternatively, the base may, like the chlorinating agent, be immobilised on a solid support. This may be achieved, for example by polymerisation of a pyridine-substituted alkene monomer such as a vinyl-di-$^t$butylpyridine monomer:

In another variation, the base may be immobilised in the same polymer chain as the acid chloride chlorinating agent. This may be achieved by polymerising a monomer which contains both an ester or anhydride functional group and a pyridine functional group. The anhydride or ester groups in the resulting polymer can be converted to acid chloride functional groups as described above. An example of this is shown below.

Conversion of the radiolabelled carboxylic acid of formula (II) to the radiolabelled acid chloride compound of formula (I) is preferably conducted by contacting the solid-phase supported chlorinating agent with a solution of the carboxylic acid.

It is greatly preferred to carry out the reaction by passing the solution of the compound of formula (II) through a column packed with a resin containing the solid phase supported chlorinating agent.

The solution may contain a base or, alternatively, a base may immobilised on a solid support as described above.

In a preferred embodiment of the invention, the radiolabelled acid chloride intermediate is radiolabelled with a radioactive imaging moiety. The term "radioactive imaging moiety" in the context of the present invention is taken to mean a radioactive isotope that may be detected external to the human body in a non-invasive manner following its administration in vivo. Examples of suitable radioactive imaging moieties of the present invention are:
  (i) a positron-emitting radioactive non-metal selected from $^{11}$C, $^{13}$N, $^{17}$F, $^{18}$F, $^{75}$Br, $^{76}$Br and $^{124}$I; or
  (ii) a gamma-emitting radioactive halogen selected from $^{123}$I, $^{125}$I, $^{131}$I or $^{77}$Br.

A preferred radioactive imaging moiety of the invention is a positron-emitting radioactive non-metal selected from $^{11}$C, $^{13}$N and $^{18}$F. These radioactive imaging moieties are particularly well suited for use as radiopharmaceuticals due to their physical and biochemical characteristics. In particular, the relatively short half-lives of these radioactive imaging moieties means that radiation exposure to a patient undergoing a PET scan is minimised. It follows that shortening the time taken to produce radiopharmaceuticals comprising such radioactive imaging moieties is particularly advantageous.

When the radioactive imaging moiety of the invention is $^{11}$C, it is preferably an inherent part of the radiolabelled acid chloride intermediate. Thus, the radiolabelled carboxylic acid of formula (II) is preferably of the formula R—$^{11}$COOH and the radiolabelled acid chloride compound of formula (I) is preferably of the formula R—$^{11}$COCl.

$^{11}$C may be produced by proton bombardment of natural nitrogen through the $^{14}$N(p,α)$^{11}$C nuclear reaction using a target gas mixture of 2% oxygen in nitrogen to produce radioactive carbon dioxide ($^{11}$CO$_2$). The $^{11}$CO$_2$ may then be reacted with Grignard reagent to give R—$^{11}$COOH and these steps may also form part of the process of the invention.

Next, a solution comprising R—$^{11}$COOH and any remaining Grignard reagent is passed through a column containing the solid-supported acyl chloride of Formula (III). An exchange reaction occurs between the excess solid-supported acyl chloride and the compound of formula (II), R—$^{11}$COOH to produce a solution of the compound of formula (I), R—$^{11}$COCl.

The compound of formula (I) is useful as an intermediate in the preparation of radiolabelled products.

Therefore, the method of the invention may include the additional step of preparing a radiolabelled amide, amine or ester by reacting a radiolabelled acid chloride compound of formula (I) as described above with an appropriate reagent.

The reaction schemes below show reactions of $^{11}$C-labelled acid chlorides of formula (I) but they are also applicable to reaction schemes below are also illustrative of the equivalent non-radioactive reactions.

Radiolabelled amides may be obtained by the following reaction:

wherein R is as defined previously; and

R' and R" are each independently hydrogen, $C_1$-$C_{20}$ alkyl or $C_2$-$C_{20}$ alkenyl, wherein alkyl or alkenyl groups may be substituted with one or more substituents chosen from OH, halo, amino, nitro, $C_1$-$C_6$ alkoxy, $C_3$-$C_{10}$ cycloalkyl, $C_3$-$C_{10}$ heterocyclyl, $C_4$-$C_{10}$ aryl or $C_4$-$C_{10}$ heteroaryl, and wherein one or more CH$_2$ groups of the alkyl or alkenyl chain may be replaced by an —S—, —O— or —NH— group; or R' and R" may be taken together with the N to which they are attached to form an aliphatic, aromatic or partially aromatic N-containing heterocycle having 5 to 30 ring atoms and up to 6 rings, which may contain one or more additional heteroatoms selected from N, O and S or in which a ring CH$_2$ may be replaced by C=O and which may be substituted with one or more substituents selected from $C_1$-$C_{20}$ alkyl, $C_2$-$C_{20}$ alkenyl, OH, halo, amino, nitro, $C_1$-$C_6$ alkoxy, $C_3$-$C_{10}$ cycloalkyl, $C_3$-$C_{10}$ heterocyclyl, $C_4$-$C_{10}$ aryl or $C_4$-$C_{10}$ heteroaryl.

The corresponding radiolabelled amines can be formed by the reduction of the radiolabelled amides by lithium aluminum hydride (LiAlH$_4$) as follows:

wherein R, R' and R" are as defined previously.

Certain radiolabelled amines can be prepared directly from the R—$^{11}$COCl, for example [$^{11}$C]-cyclopentyltheophyline [Yorke et al 1994 J. Label. Compd. Radiopharm.35 pp 262-3]:

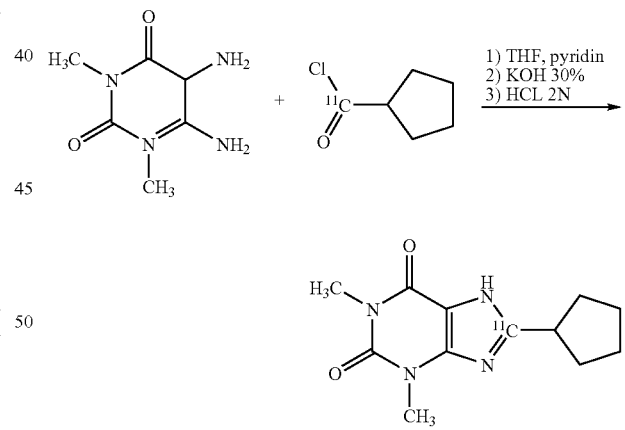

Radiolabelled esters may be obtained by the following reaction:

wherein R is as defined previously and R'" is a group as defined previously for R' and R".

Preferably, the radiolabelled product is a radiopharmaceutical, preferred examples [including references to prior art methods of synthesis] of which are given in Table 1.

TABLE 1

Structures of preferred radiopharmaceuticals of the invention

| Radiopharmaceutical | Structure | Prior art reference |
|---|---|---|
| [carbonyl-$^{11}$C]-WAY-100635 | 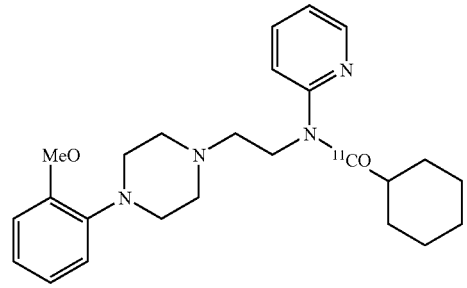 | McCarron et al 1996 J. Label. Compd. Radiopharm. 38 pp 941-53 |
| [$^{11}$C]-propyl-norapomorphine | 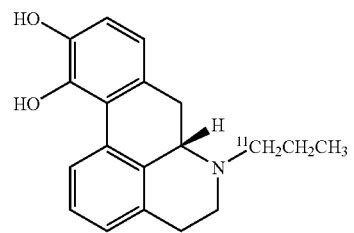 | Hwang et al 2000 Nucl Med Biol. 27(6) pp 533-9 |
| [$^{11}$C]-diprenorphine | 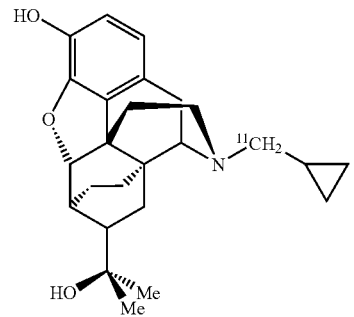 | Luthra et al 1985 J. Chem. Soc. Comm. 70 pp 1423-5 |
| [$^{11}$C]-buprenorphine | 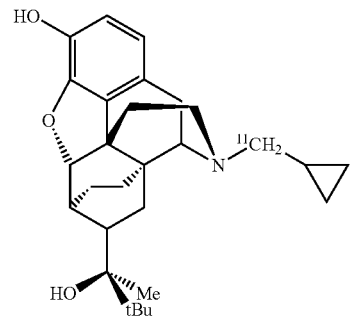 | Luthra et al 1987 Appl. Radiat. Isot. 38 pp 65-6 |
| [$^{11}$C]-cyclopentyltheophylline | 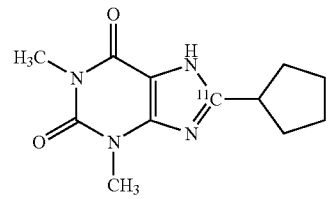 | Yorke et al 1994 J. Label. Compd. Radiopharm. 35 pp 262-3 |

In a further aspect the present invention relates to a kit for carrying out the method of the invention comprising:

(i) a first cartridge containing a solid-phase supported chlorinating agent; and, (ii) a vial containing a solution suitable for dissolving the radiolabelled carboxylic acid of formula (II), or components which can be reconstituted to form such a solution. The dissolved radiolabelled carboxylic acid of formula (II) is passed through the cartridge wherein it reacts with the solid-phase supported chlorinating agent to form the radiolabelled acid chloride of formula (I).

The solution for dissolving the radiolabelled carboxylic acid of formula (II) may also contain a base, for example a pyridine base such as di-$^t$butoxypyridine. Alternatively, the first cartridge may contain a solid-phase supported base, which may be a polymer as defined above.

Suitable solid-supported chlorinating agents and bases are as defined above in relation to the first aspect of the invention.

In another aspect, the present invention relates to a kit for the radiosynthesis of a radiolabelled product comprising the kit for carrying out the method of the invention and:

i) a second cartridge containing a solid-phase supported non-radioactive precursor of the radiolabelled product.

In use, the radiolabelled acid chloride of formula I is passed through the second cartridge where it reacts with the solid-phase supported non-radioactive precursor of the radiolabelled product to form the radiolabelled product.

Non-radioactive precursors of amines, amides and esters are described above.

BRIEF DESCRIPTION OF THE EXAMPLES

Example 1 describes how a polystyrene-supported acyl chloride is obtained.

Example 2 describes the radiosynthesis of a [$^{11}$C]-acid chloride.

Example 3 describes the radiosynthesis of a [$^{11}$C]-amide.

Example 4 describes the radiosynthesis of a [$^{11}$C]-amine.

EXAMPLES

Example 1

Preparation of Polystyrene-Supported Acyl Chloride

Polystyrene-supported carboxylic acid [Novabiochem Cat. No. 01-64-0111] is converted to polystyrene-supported acyl chloride by treatment with either oxalyl chloride or thionyl chloride by methods disclosed in the prior art [Leznoff et al 1977 Can. J. Chem. 55 p 3351-, Meyers et al 1995 Molecular Diversity 1 p 13].

Example 2

Radiosynthesis of An [$^{11}$C]-Acid Chloride

A solution of [$^{11}$C]-labelled carboxylic acid and Grignard reagent is passed through a column containing polystyrene-supported acyl chloride. An exchange reaction occurs between the excess polystyrene-supported acyl chloride and the no carrier added carboxylic acid to produce a solution of [$^{11}$C]-labelled acid chloride.

Example 3

Radiosynthesis of A [$^{11}$C]-Amide

The solution of [$^{11}$C]-labelled acid chloride produced in Example 2 is reacted with a secondary amine to obtain the respective [$^{11}$C]-labelled amide product.

Example 4

Radiosynthesis of A [$^{11}$C]-Amine

The [$^{11}$C]-labelled amide product obtained in Example 3 is reduced in the presence of lithium aluminum hydride (LiAlH$_4$) to obtain the respective [$^{11}$C]-labelled amine.

Example 5

Radiosynthesis of A [$^{11}$C]-Ester

The [$^{11}$C]-labelled acid chloride of Example 2 is reacted with an alcohol in the presence of pyridine or NaOH to obtain the respective [$^{11}$C]-labelled ester.

What is claimed is:

1. A method for the preparation of a $^{11}$C radiolabelled acid chloride compound of formula (I):

$$R\text{---}^{11}COCl \qquad (I)$$

wherein R is C$_1$-C$_{20}$ alkyl, C$_2$-C$_{20}$ alkenyl, C$_3$-C$_{10}$ cycloalkyl, C$_3$-C$_{10}$ heterocyclyl, C$_4$-C$_{10}$ aryl or C$_4$-C$_{10}$ heteroaryl, any of which may optionally be substituted with NO$_2$, —O(C$_1$-C$_6$ alkyl), C$_3$-C$_{10}$ cycloalkyl or C$_4$-C$_{10}$ aryl;

the method comprising reacting a $^{11}$C radiolabelled carboxylic acid of formula (II):

$$R\text{---}^{11}COOH \qquad (II)$$

wherein R is as defined for formula (I);

with a solid-phase supported chlorinating agent in the presence of a base, wherein the solid-phase supported chlorinating agent is a solid-phase supported acyl chloride of formula III:

$$[\text{solid support}]\text{---linker---COCl} \qquad (III)$$

wherein the linker is a polyethylene glycol linker or comprises up to four groups selected from:

C$_4$-C$_{10}$ aryl or C$_4$-C$_{10}$ heteroaryl groups;

(CH$_2$)$_x$ groups where x is an integer from 1 to 20;

(CH$_2$)$_y$—O—(CH$_2$)$_z$ groups where y and z are integers from 1 to 20;

or combinations thereof;

wherein, in the linker groups, any CH$_2$ group may be replaced by —O—, —S—, —SO$_2$— or —NH$_2$— and the linker groups may be substituted with one or more substituents chosen from OH, halo, amino, nitro and C$_1$-C$_6$ alkoxy.

2. A method as claimed in claim 1, wherein the solid phase supported chlorinating agent comprises a chlorinating agent connected by a linker to a solid support.

3. A method as claimed in claim 2, wherein the solid support is a polymer or comprises small discrete particles.

4. A method as claimed in claim 2 wherein the solid support comprises a coating on the inner surface of a cartridge or a microfabricated vessel.

5. A method as claimed in claim 3, wherein the polymer is polystyrene, polyacrylamide or polypropylene.

6. A method as claimed in claim 2, wherein the solid-phase supported chlorinating agent is a solid-phase supported acid chloride, or a solid-phase supported analogue of either thionyl chloride or oxalyl chloride.

7. A method as claimed in claim 1, wherein the solid-phase supported acyl chloride is of Formula IIIa:

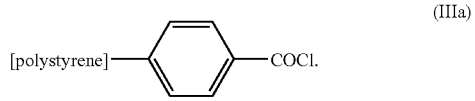

(IIIa)

8. A method as claimed in claim 1, wherein the solid phase supported chlorinating agent is an integral part of a polymer.

9. A method as claimed in claim 8 wherein the solid-phase supported chlorinating agent comprises a polymer having one or two acid chloride groups on every unit.

10. A method as claimed in claim 9 wherein the solid-phase supported chlorinating agent is prepared by polymerisation of a monomer containing an acid anhydride or an ester group to give a polymer which contains an anhydride or ester group on every unit, followed by conversion of each of the anhydride or ester groups to acid chloride groups.

11. A method as claimed in claim 1, wherein the base is a pyridine derivative.

12. A method as claimed in claim 11, wherein the base is immobilised on a solid support.

13. A method as claimed in claim 12 wherein the base is prepared by polymersiation of a pyridine-substituted alkene monomer.

14. A method as claimed in claim 13 wherein the acid chloride chlorinating agent and the base are immobilised in the same polymer chain.

15. A method as claimed in claim 1, wherein the solid-phase supported chlorinating agent is contacted with a solution of the radiolabelled carboxylic acid of formula (II).

16. A method as claimed in claim 15, wherein the solution of the compound of formula (II) is passed through a column packed with a resin containing the solid phase supported chlorinating agent.

17. A method as claimed in claim 1, wherein the radiolabelled acid chloride of formula (I) is radiolabelled with a radioactive imaging moiety selected from:
(i) a positron-emitting radioactive non-metal selected from $^{11}C$, $^{13}N$, $^{17}F$, $^{18}F$, $^{75}Br$, $^{76}Br$ and $^{124}I$; or
(ii) a gamma-emitting radioactive halogen selected from $^{123}I$, $^{125}I$, $^{131}I$ or $^{77}Br$.

18. A method as claimed in claim 17 wherein the radiolabelled acid chloride of formula (I) is radiolabelled with $^{11}C$, $^{13}N$ or $^{18}F$.

19. A method as claimed in claim 18 wherein the radiolabelled carboxylic acid of formula (II) is of the formula R—$^{11}COOH$ and the radiolabelled acid chloride compound of formula (I) is of the formula R—$^{11}COCl$.

20. A method as claimed in claim 19, further comprising the initial steps of:
(i) producing $^{11}CO_2$ by proton bombardment of natural nitrogen through the $^{14}N(p,\alpha)^{11}C$ nuclear reaction using a target gas mixture of 2% oxygen in nitrogen; and
(ii) reacting the $^{11}CO_2$ with Grignard reagent to give R—$^{11}COOH$.

21. A method as claimed in claim 1, further including the additional step of converting the radiolabelled acid chloride compound of formula (I) to a radiolabelled amide of formula:

R—$^{11}CONR'R''$ wherein R is as defined in claim 1; and

R' and R'' are each independently hydrogen, $C_1$-$C_{20}$ alkyl or $C_2$-$C_{20}$ alkenyl, wherein alkyl or alkenyl groups may be substituted with one or more substituents chosen from OH, halo, amino, nitro, $C_1$-$C_6$ alkoxy, $C_3$-$C_{10}$ cycloalkyl, $C_3$-$C_{10}$ heterocyclyl, $C_4$-$C_{10}$ aryl or $C_4$-$C_{10}$ heteroaryl, and wherein one or more $CH_2$ groups of the alkyl or alkenyl chain may be replaced by an —S—, —O— or —NH— group; or R' and R'' may be taken together with the N to which they are attached to form an aliphatic, aromatic or partially aromatic N-containing heterocycle having 5 to 30 ring atoms and up to 6 rings, which may contain one or more additional heteroatoms selected from N, O and S or in which a ring $CH_2$ may be replaced by C=O and which may be substituted with one or more substituents selected from $C_1$-$C_{20}$ alkyl, $C_2$-$C_{20}$ alkenyl, OH, halo, amino, nitro, $C_1$-$C_6$ alkoxy, $C_3$-$C_{10}$ cycloalkyl, $C_3$-$C_{10}$ heterocyclyl, $C_4$-$C_{10}$ aryl or $C_4$-$C_{10}$ heteroaryl;

by reaction with an amine of formula:

R'R''—NH wherein R' and R'' are as defined above.

22. A method as claimed in claim 21, further comprising converting the radiolabelled amide to a radiolabelled amine of formula:

R—$^{11}CH_2N$—R'R'' by reduction with lithium aluminium hydride, wherein R is as defined in claim 1; and R' and R'' are each independently hydrogen $C_1$-$C_{20}$ alkyl or $C_2$-$C_{20}$ alkenyl, wherein alkyl or alkenyl groups may be substituted with one or more substituents chosen from OH, halo, amino nitro, $C_1$-$C_6$ alkoxy, $C_3$-$C_{10}$ cycloalkyl, $C_3$-$C_{10}$ heterocyclyl, $C_4$-$C_{10}$ aryl or $C_4$-$C_{10}$ heteroaryl, and wherein one or more $CH_2$ groups of the alkyl or alkenyl chain may be replaced by an —S—, —O— or —NH— group; or R' and R'' may be taken together with the N to which they are attached to form an aliphatic, aromatic or partially aromatic N-containing heterocycle having 5 to 30 ring atoms and up to 6 rings which may contain one or more additional heteroatoms selected from N, O and S or in which a ring $CH_2$ may be replaced by C=O and which may be substituted with one or more substituents selected from $C_1$-$C_{20}$ alkyl, $C_2$-$C_{20}$ alkenyl, OH, halo, amino, nitro, $C_1$-$C_6$ alkoxy, $C_3$-$C_{10}$ cycloalkyl, $C_3$-$C_{10}$ heterocyclyl, $C_4$-$C_{10}$ aryl or $C_4$-$C_{10}$ heteroaryl.

23. A method as claimed in claim 1, further comprising the step of converting the radiolabelled acid chloride compound of formula (I) to a radiolabelled ester of formula:

R—$^{11}CO_2R'''$ by reaction with a compound of the formula:

R—$CO_2R'''$ wherein R is as defined in claim 1 and R', R'' and R''' are each independently hydrogen, $C_1$-$C_{20}$ alkyl or $C_2$-$C_{20}$ alkenyl, wherein alkyl or alkenyl groups may be substituted with one or more substituents chosen from OH, halo, amino, nitro, $C_1$-$C_6$ alkoxy, $C_3$-$C_{10}$ cycloalkyl, $C_3C_{10}$ heterocyclyl, $C_4$-$C_{10}$ aryl or $C_4$-$C_{10}$ heteroaryl, and wherein one or more $CH_2$ groups of the alkyl or alkenyl chain may be replaced by an —S—, —O— or —NH— group; or R', R'' and R''' may be taken together with the N to which they are attached to form an aliphatic, aromatic or partially aromatic N-containing heterocycle having 5 to 30 ring atoms and up to 6 rings which may contain one or more additional heteroatoms selected from N, O and S or in which a ring $CH_2$ may be replaced by C=O and which may be substituted with one or more substituents selected from $C_1$-$C_{20}$ alkyl, $C_2$-$C_{20}$ alkenyl, OH, halo, amino, nitro, $C_1$-$C_6$ alkoxy, $C_3$-$C_{10}$ cycloalkyl, $C_3$-$C_{10}$ heterocyclyl, $C_4$-$C_{10}$ aryl or $c_4$-$C_{10}$ heteroaryl.

* * * * *